United States Patent [19]

Billington et al.

[11] Patent Number: 4,797,431
[45] Date of Patent: Jan. 10, 1989

[54] GLASS/POLY(CARBOXYLIC ACID) CEMENT COMPOSITIONS

[75] Inventors: Richard W. Billington, London; Jill A. Williams, Thorpe, both of England

[73] Assignee: Dentsply Limited, Weybridge, England

[21] Appl. No.: 34,880

[22] Filed: Apr. 6, 1987

[30] Foreign Application Priority Data

Apr. 18, 1986 [GB] United Kingdom ............... 8608546

[51] Int. Cl.$^4$ ............................................. A61K 5/06
[52] U.S. Cl. ...................................... 523/116; 523/117
[58] Field of Search ................................. 523/116, 117

[56] References Cited

U.S. PATENT DOCUMENTS

| | | | |
|---|---|---|---|
| Re. 32,073 | 1/1986 | Randklev | 523/117 |
| 3,971,754 | 7/1976 | Jurecic | 523/117 |
| 4,032,504 | 6/1977 | Lee, Jr. et al. | |
| 4,215,033 | 7/1980 | Bowen | |
| 4,217,264 | 8/1980 | Mabie et al. | 524/405 |
| 4,492,777 | 1/1985 | Denton, Jr. et al. | |

FOREIGN PATENT DOCUMENTS

| | | |
|---|---|---|
| 3000118 | 7/1980 | Fed. Rep. of Germany . |
| 2246589 | 5/1975 | France . |
| 80/00409 | 3/1980 | PCT Int'l Appl. . |

*Primary Examiner*—Herbert J. Lilling
*Attorney, Agent, or Firm*—Edward J. Hanson, Jr.; David E. Wheeler

[57] ABSTRACT

A process for producing a radiopaque cement comprises reacting a polymer containing free carboxyl groups (generally a homo or copolymer of acrylic acid) with a particulate acid-leachable source of polyvalent metal ions (such as an acid-leachable glass) in the presence of water and strontium fluoride.

8 Claims, No Drawings

GLASS/POLY(CARBOXYLIC ACID) CEMENT COMPOSITIONS

This invention is concerned with improvements in and relating to glass/poly(carboxylic acid) compositions.

Glass/poly(carboxylic acid) cement compositions are well known and established. Such compositions basically comprise (i) a polymer containing free carboxylic acid groups (typically a homo- or co-polymer of acrylic acid) and (ii) an acid leachable source of polyvalent metal ions (e.g. an acid leachable glass such as a calcium aluminofluorosilicate glass). In the presence of water, the polyacid leaches polyvalent metal ions from the source thereof and these serve to cross-link the polymer chains to give a solid material (a cement). Such compositions are discussed authoritatively in, for example, "Organolithic Macromolecular Materials" by A.D. Wilson and S. Crisp, Applied Science Publishers, 1977 (see especially Chapter 4).

Glass/poly(carboxylic acid) cement compositions have been found to have particular application as dental restorative materials but suffer from one practical disadvantage in that they are radiolucent, that is they are essentially transparent to X-rays. As a result, it is not possible for, for example, to examine a dental restoration, carried out using such a composition, by means of an X-ray technique and, further, it is not possible to locate any portion of a dental restoration which may become dislodged and ingested by a person, using an X-ray technique.

The radiopacity of tooth substances (i.e. the degree to which they absorb X-rays) may conveniently be defined in terms of the thickness (in mm) of aluminium having the same radiopacity as 1 mm of the substance. Typical values for enamel are 1.3–2.7 mm aluminium per mm enamel and for dentine, 0.6–2.0 mm aluminium per mm dentine.

It has now been found, in accordance with the present invention, that a radiopaque cement may be formed from a composition comprising a polymer containing free carboxyl groups, an acid leachable source of polyvalent metal ions and water, and also containing strontium fluoride. Strontium fluoride is the principal radiopacifying agent present providing substantially all the radiopaque properties even in the presence of other materials having some radiopacifying properties.

It has further been found that the use of strontium fluoride gives an optically transparent set cement (similar to the set cement obtained in the absence strontium fluoride), which renders the set cement of the invention of value in dental restoration. Expressed in terms of the $C_{0.70}$ value, the translucency is suitably less than 0.7, preferably less than 0.6 and most preferably less than 0.5.

According to the invention, therefore, there is provided a method of producing a cross-linked cement which comprises reacting a polymer containing free carboxyl groups with a particulate acid or alkali-leachable source of polyvalent metal ions in the presence of water and strontium fluoride.

In order to achieve acceptable radiopacity in use, the strontium fluoride is suitably present in an amount of from 7.5 to 50%, preferably 15 to 33%, and more preferably 19 to 23%, by weight, based on the total weight of the polymer containing free carboxyl groups, the acid leachable source of polyvalent metal ions and the strontium fluoride.

The source of polyvalent metal ions may, for example, be an acid-leachable glass such as a calcium aluminofluorosilicate glass, preferably comprising: calcium (calculated as CaO) 9 to 25% by weight; aluminium (calculated as $Al_2O_3$), 28 to 38%, by weight; silica (calculated as $SiO_2$) 25 to 30% by weight; and fluorine (calculated as $F_2$), 0 to 12% by weight; and phosphorus (calculated as $P_2O_5$), 0 to 9% by weight. For the sake of convenience the source of polyvalent metal ions will hereinafter simply be referred to as a "glass". As will be appreciated strontium fluoride itself may serve as a source of polyvalent metal ions.

The polymer containing free carboxyl groups is preferably a homopolymer of acrylic acid. Copolymers of acrylic acid, may be used but are less suitable (see D.J. Setchell et al, British Dental Journal, 1985, Vol. 158: Vol. page 220). The acrylic acid polymer or copolymer suitably has a molecular weight of 20,000 to 125,000, preferably 35,000 to 70,000, and most preferably 45,000 to 55,000. For the sake of convenience the polymer containing free carboxylic acids will hereinafter simply be referred to as a "polyacrylic acid".

The glass should be in particulate form and suitably has a particle size of from 0.5 to 60 $\mu$m. The particle size of the glass may vary within these limits depending upon the intended end use of the composition. Thus, for example, where the composition is to be used as a simple dental restorative material (i.e. as a filling or stopping material) the particle size is suitably from 0.5 to 40 $\mu$m, preferably 1 to 30 $\mu$m, and most preferably 2 to 20 $\mu$m; and when intended for use as a sub-filling, base or liner under a so-called "composite" dental restorative material (i.e. a mixture of an ethylenically unsaturated resinous material, an inert particulate filler and a curing agent for the resinous material), the particle size is suitably 2 to 60 $\mu$m, preferably 2 to 40 $\mu$m and most preferably 5 to 30 $\mu$m.

The weight ratio of polyacrylic acid to glass is suitably from 0.15:1 to 0.5:1, preferably 0.2:1 to 0.3:1; and the weight ratio of water to glass is suitably from 0.2:1 to 0.5:1, preferably about 0.25:1.

The reaction of the polyacrylic acid and glass may be carried out in the presence of other materials serving to alter or modify the working time and/or setting time of the mixture, e.g. a hydroxycarboxylic acid such as tartaric acid which serves to increase the rate of set of the composition without effecting the working time.

Compositions for forming a solid cement from glass, polyacrylic acid and strontium fluoride may be put up as two-part packs, one part comprising an aqueous solution of the polyacrylic acid (and optionally working/setting time modifiers) and the other part comprising a particulate glass together with strontium fluoride. Alternatively, a dry blend may be formed of particulate glass and a powdered polymer and strontium fluoride for subsequent addition of water to form a cement-forming composition.

Cements formed in accordance with the invention are generally radiopaque and we have found that they are eminently suitable as base-fillings, bases or liners for use in under the so-called composite filling materials discussed above.

A wide variety of such composite filling materials are known or have been proposed. Those in more common use comprise a polyethylenically unsaturated monomer or oligomer (e.g. bis-GMA or a derivative thereof or a urethane diacrylate), an ethylenically unsaturated component (e.g. ethylene glycol dimethacrylate), a filler and a polymerization initiator. Typical fillers are particulate quartz, borosilicate glasses or glass ceramics having a particle size of from 1 to 80 μm, and/or colloidal silica having a particle size of 0.005 to 0.2 μm. The polymerization initiator may be a heat room temperature acting initiator, such as benzoyl peroxide and a tertiary amine, or may be an actinic radiation sensitive initiator such as benzophenone or camphorquinone.

In accordance with a further embodiment of the invention, therefore, there is provided a method of dental restoration which comprises forming a base, liner or sub-filling in accordance with the method of the invention and subsequently forming an overlying filling, on the base, from a composite dental composition comprising one or more ethylenically unsaturated compounds, a particular filler and a polymerization initiator for the ethylenically unsaturated compound(s).

Strontium fluoride may be used, in accordance with the invention, as radiopacifying agent in other dental resorative materials, e.g. in composite type materials as discussed above. In particular, strontium fluoride may be used in composite filling materials and in pit and tissue sealants where the caries inhibiting effect of fluoride in ion is particularly desirable and the radiopacifying effects of strontium fluoride may assist in the diagnosis of recurrent caries.

In a broader aspect the invention provides a resinous structure containing strontium as a radiopacifying agent, preferably the principal or only such agent. Such a structure, which is preferably translucent, suitably has a radiopacity of at least 1.0 mm of aluminium per mm of structure, preferably at least 1.5 mm, most preferably at least 2.0 mm of aluminium per mm of structure. Such a structure is suitably used for dental restorative procedures.

In order that the invention may be well understood the following Examples are given by way of illustration only. In the Examples all percentages are by weight unless otherwise stated.

EXAMPLE 1

A cement-forming powder was prepared from (a) 62.1% by weight of a particulate calcium fluoroaluminosilicate glass (commercially available as Chemfil II) having a Sauter Mean Diameter of 5 μm. (b) 15.1% of a polyacrylic acid powder having a molecular weight of 45,000, (c) 1.3% of tartaric acid, and (d) 21.5% of strontium fluoride.

The powder was mixed with water, by hand using a dental spatula and a glass block, at a powder/water ratio of 6.8:1. The resulting cement typically had a working time at 23° C. of 2 minutes, a radiopacity of 2.5 mm aluminium per 1 mm cement, a compressive strength of 182 MPa, a diametral strength of 15.3 MPa and a solubility of 0.25%.

EXAMPLE 2

A powder was prepared as described in Example 1 except that it contained 69.3% of the powdered glass and 14.3% of strontium fluoride. The powder was evaluated as described in Example 1 and was found to have a typical working time of 2 minutes at 23° C., a compressive strength of 204 MPa, and a radiopacity of 1.5 mm per 1 mm cement.

EXAMPLE 3

10 Grams of a resin comprising 5 parts of the urethane adduct of 2 moles of hydroxypropyl methacrylate and tri-methylhexamethylene diisocyanate are dissolved in 10 grams of triethylene glycol dimethacrylate. They are then dissolved in the solution, 0.03 g of camphorquinone and 0.2 g of methyldiethanolamine; and finally, 15 g of strontium fluoride having a particle size less than 10 μ m is dispersed in the solution. The resulting composition is polymerized by actinic radiation using a Prismalite (product of L.D. Caulk Division, Dentsply Inc.) using 20 seconds of irradiation, to provide a radiopaque composition suitable for sealing pits and fissures.

We claim:

1. A substantially optically translucent dental restorative material comprising a polymerized matrix containing an acid or an alkali-leachable source of polyvalent metal ions, said matrix consisting essentially of a homopolymer or copolymer of acrylic acid having a molecular weight of 20,000 to 125,000 and said leachable source consisting essentially of by weight about 15–33% $SrF_2$, not more than 25% CaO, 28–38% $Al_2O_3$, 25–30% $SiO_2$, 0–9% $P_2O_5$, the ratio of said homopolymer to said leachable source being between 0.15 to 1 and 0.5 to 1 whereby the strontium fluoride provides essentially all of the radiopaque properties.

2. The dental restorative material of claim 1 in which said homopolymer comprises ethylenically unsaturated compounds, said leachable source comprises a particulate filler.

3. The dental restorative material of claim 2 in which the polymerized matrix is formed from a composite composition comprising ethylenically unsaturated compounds, particulate filler and polymerization initiator.

4. The restorative material of claim 3 which is a polyacrylate dental cement.

5. A structure as claimed in claim 1 having a radiopacity of at least 1.0 mm of aluminium per mm of structure.

6. A structure as claimed in claim 1 having a radiopacity of at least 1.5 mm aluminium per mm of structure.

7. A structure as claimed in claim 1 having a radiopacity of at least 2.0 mm aluminium per mm of structure.

8. The homopolymer of claim 1 having a molecular weight of from 35,000 to 70,000.

* * * * *